United States Patent [19]

Clack

[11] 4,245,914

[45] Jan. 20, 1981

[54] SAMPLE CELL WINDOW CLEANING DEVICE

[75] Inventor: Peter J. Clack, Doylestown, Pa.

[73] Assignee: Leeds & Northrup Company, North Wales, Pa.

[21] Appl. No.: 138,012

[22] Filed: Apr. 7, 1980

[51] Int. Cl.³ .............................................. G01N 35/00

[52] U.S. Cl. ...................................... 356/440; 350/61; 356/246

[58] Field of Search ................ 356/246, 436, 440–442; 350/61, 63; 250/573–577

[56] References Cited

U.S. PATENT DOCUMENTS

| | | | |
|---|---|---|---|
| 4,165,179 | 8/1979 | Sato | 356/246 |
| 4,167,335 | 9/1979 | Williams | 356/336 |

*Primary Examiner*—John K. Corbin

*Assistant Examiner*—Bruce Y. Arnold

*Attorney, Agent, or Firm*—Raymond F. MacKay; William G. Miller, Jr.

[57] ABSTRACT

Apparatus for wiping the optical window of a sample cell in a turbidimeter or other particle measuring instrument for analyzing a liquid sample. The wiping apparatus is operated by the pressure of the source of supply of the liquid sample and avoids the necessity of liquid seal bearings.

5 Claims, 3 Drawing Figures

SAMPLE CELL WINDOW CLEANING DEVICE

BACKGROUND OF THE INVENTION

When using particle analysis equipment such as turbidimeters with flow through cells in industrial applications, the build-up of material on the optical windows of the cell can seriously degrade performance. In the past, manual cleaning systems have been relied upon which generally are inconvenient in many instruments. Also, there have been proposed automated systems utilizing electrically or hydraulically operated cleaning devices. In those situations the hydraulic or electric material has been located externally of the cell and required a liquid seal where the motion required by the cleaning device passed through the wall of the sample cell.

SUMMARY OF THE INVENTION

An object of the present invention is to provide a cell cleaning device, the moving parts of which are located within the sample cell chamber and therefore avoids the necessity of any packing or sealing between the cleaning device and the sample cell. Furthermore, the motor power for the cleaning device is derived from the pressure of the sample to be analyzed. The device for wiping the optical window provided by the present invention can be operated to give a thorough wiping to the inner surface of the sample cell window without requiring the measuring instrument to be disassembled. Thus, it permits the wiping operation to be carried out quickly and perfectly.

Other objects and characteristic features of the present invention will become apparent from the description to be given in detail hereinbelow with reference to the accompanying drawings.

DESCRIPTION OF THE PREFERRED EMBODIMENT

Figure 1:
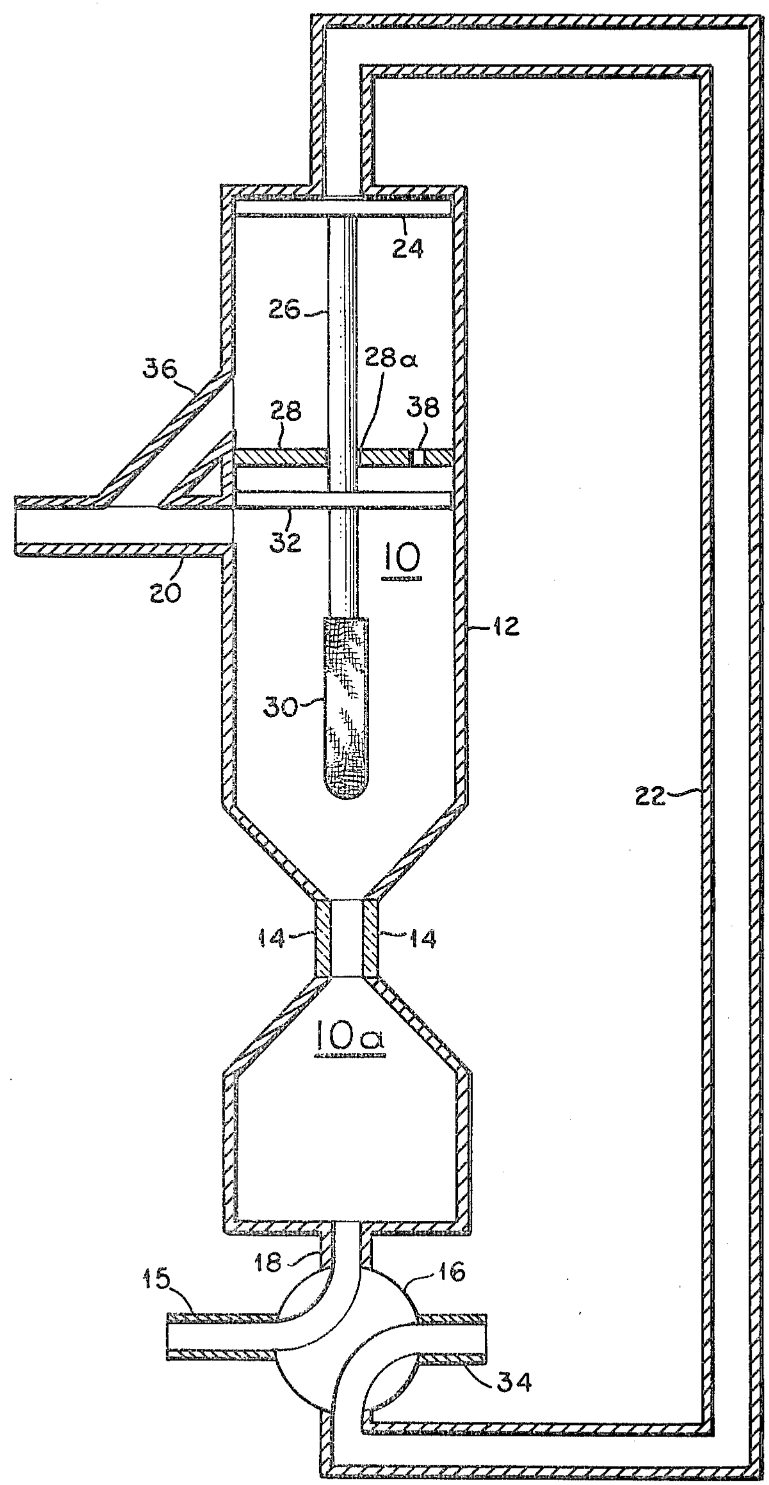
FIG. 1 is a sectional side view illustrating schematically a liquid sample cell with the cell cleaning structure in a withdrawn position.

In FIG. 1 there is shown a sample cell, or elongated chamber, 10 of the type used for a particle measuring system as described in U.S. Pat. No. 4,167,335 which issued to Frederick L. Williams on Sept. 11, 1979 for a volume loading measurement utilizing particle scattering. The side walls 12 of the sample cell 10 are shown as being constricted to form a restricted area 10*a*. Located on opposite sides of the restricted area 10*a* are a pair of windows 14,14 to allow for the passage of light through the cell 10 and any liquid sample flowing therethrough for purposes of analyzing a characteristic of the liquid sample.

Figure 2:
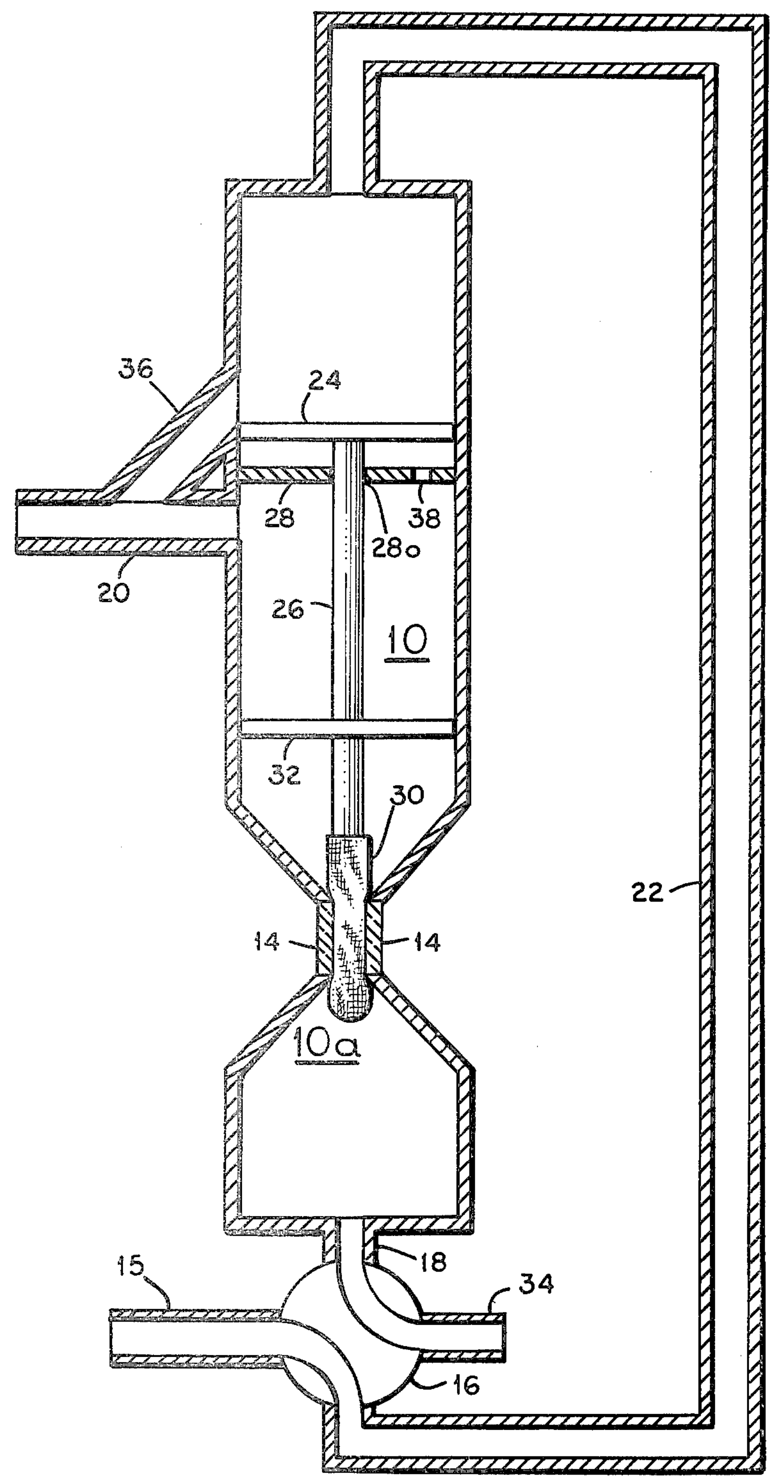
FIG. 2 is a sectional side view of a liquid sample cell with the cell cleaning structure in a cleaning position.

As shown in FIG. 1, the liquid sample to be analyzed is supplied from a source, not shown, through a pipe 15, a valve 16 and an inlet pipe 18 to the bottom portion of the sample cell 10. With the valve 16 in the position shown, the sample flows through the cell 10 and discharges through an outlet pipe 20. When the windows 14,14 become soiled by contaminants contained in the liquid flowing through the sample cell 10 or for any other reason, the valve 16 may be rotated from the position shown in FIG. 1 to the position as shown in FIG. 2. With the valve 16 in the position as shown in FIG. 2, the liquid sample introduced at the pipe 15 flows by way of the valve 16 and the pipe 22 to the upper end portion of the sample cell 10. With the liquid sample applied to the upper end of the sample cell 10, there is applied to the upper surface of a flexible washer 24 the pressure of the source of the liquid sample supplied by pipe 15. The flexible washer 24 is of such a size and shape that it conforms to the inner surface of the walls 12 of the sample cell 10 to provide a seal between the periphery of the washer 24 and the walls 12. The pressure of the liquid sample on the upper surface of the washer 24 produces a downward force on the washer 24 that moves the washer 24 and the rod 26 which is attached to the washer 24 in an axially downward direction. During its travel, the rod 26 is guided by an opening 28*a* in a guide wall 28 so that the rod 26 moves axially in the sample cell 10. Attached to the end of the rod 26 is a swab 30 for cleaning the inner surfaces of the windows 14,14. The swab 30 may be any suitable cleaning device such as a brush, a sponge or fabric that is preferably attached to the rod 26 by a suitable cement.

As the rod 26 and the swab 30 moves downwardly through the sample cell 20 under the influence of the pressure from the liquid applied to the upper surface of the washer 24, the swab 30 is moved into a wiping engagement with the inner surfaces of the windows 14,14 as shown in FIG. 2. Preferably the dimension of the swab 30 is slightly larger than the distance between the windows 14,14 so that a good wiping action exists between the surface of the swab 30 and the windows 14,14 to provide a high degree of cleaning action to remove the soil on the inner surfaces of the windows 14,14.

During the time that the liquid is moving the rod 26 and the swab 30 in a downward direction, a second washer 32 secured to the rod 26 and made of a soft material and of dimensions to conform to the inner wall surfaces of the sample cell 10 to provide a seal with the wall of the sample cell 10 forces the liquid from the sample cell 10 through inlet pipe 18 and the valve 16 (FIG. 2) to a waste pipe 34.

As the washer 24 is moved downward through the sample cell 10, the entrance to an outlet pipe 36 is opened to establish flow communication between the pipe 22 and the pipe 36. The liquid applied by pipe 22 to the upper portion of sample cell 10 then flows through the upper portion of the sample cell 10 and out through the outlet pipe 36 which is shown connected to the outlet pipe 20. Thus, there is only a slight interruption in the flow of the liquid sample from the inlet pipe 18 to the outlet pipe 20 as a result of the window cleaning operation.

When the swab 30 is to be moved to its withdrawn position, the valve 16 is placed in the position shown in FIG. 1, and the liquid to be sampled is again introduced into the sample cell 10 through inlet pipe 18 in the lower portion of the sample cell 10. The liquid sample flows past the swab 30 and the pressure of the liquid source is applied to the lower surface of the washer 32 to cause the washer 32 and the rod 26 to move upward to withdraw the swab 30 from its window wiping position. The pressure of the liquid on the lower surface of the washer 32 causes the plunger to rise vertically until the washer 32 uncovers the entrance to the outlet pipe 20 to establish flow communication between the pipe 18 and the pipe 20 to permit the liquid being analyzed to flow through the cell 10 between the windows 14,14 and out the outlet pipe 20. During the time that the rod 26 is moving upwards, the liquid in the upper portion of the sample cell 10 is forced out of the upper portion of the sample cell 10 by the washer 24. The liquid flows through the pipe 22, the valve 16 and out the waste pipe 34.

In order to prevent liquid from being trapped between the guide wall 28 that serves as a guide for the rod 26, and either of the washers 24 and 32, there is provided in the guide wall 28 an opening or vent 38. It is to be understood, of course, that this vent 38 may not be necessary as venting may be readily accomplished by providing an enlarged opening 28*a* through the guide wall 28 for the rod 26 that provides the necessary guiding action and at the same time provides the venting means for allowing any trapped liquid to pass through the space between the rod 26 and the wall 28.

The sample cell 10 and pipes 18, 20, 22 and 36 have been shown without identifying any particular method of assembling the apparatus as such features do not form any part of my invention. In a typical case, the sample cell 10 was constructed of brass tubing and the restricted area 10*a* of the sample cell 10 was created by pressing the side walls 12 together. Such a procedure formed substantially rectangular flat areas in the side walls 12 of the sample cell 10 to permit the mounting therein of corresponding flat windows 14,14. In another embodiment the upper and lower portions of the sample cell 10 were made in two sections that were threaded together for ease of assembly.

It is to be understood that the cross-sectional area of the sample cell 10 in the restricted areas 10*a* may be rectangular in shape. In such a case, it is desirable that the swab 30 have a rectangular cross-section and that the angular orientation of the swab 30 with respect to the restricted area 10*a* be maintained as the rod 26 is moved from a withdrawn position to a window cleaning position. If such alignment is critical, the rod 26 would be of a non-circular cross-sectional shape corresponding with a similar shaped opening 28*a* in the guide wall 28 so as to at all times maintain the swab 30 properly oriented with respect to the windows 14,14. If the cell arrangement is such that a cylindrical swab 30 may be used, then the guide hole 28*a* in the guide wall 28 may be arranged to cooperate with the rod 26 in such a way that the swab 30 not only undergoes translational movement but also rotation as it moves longitudinally in the sample cell 10 from the restricted position to the cell cleaning position. Such an arrangement may be easily provided by a helical groove, not shown, in the rod 26 and a cooperating pin fixedly mounted on the guide wall 28.

Figure 3:
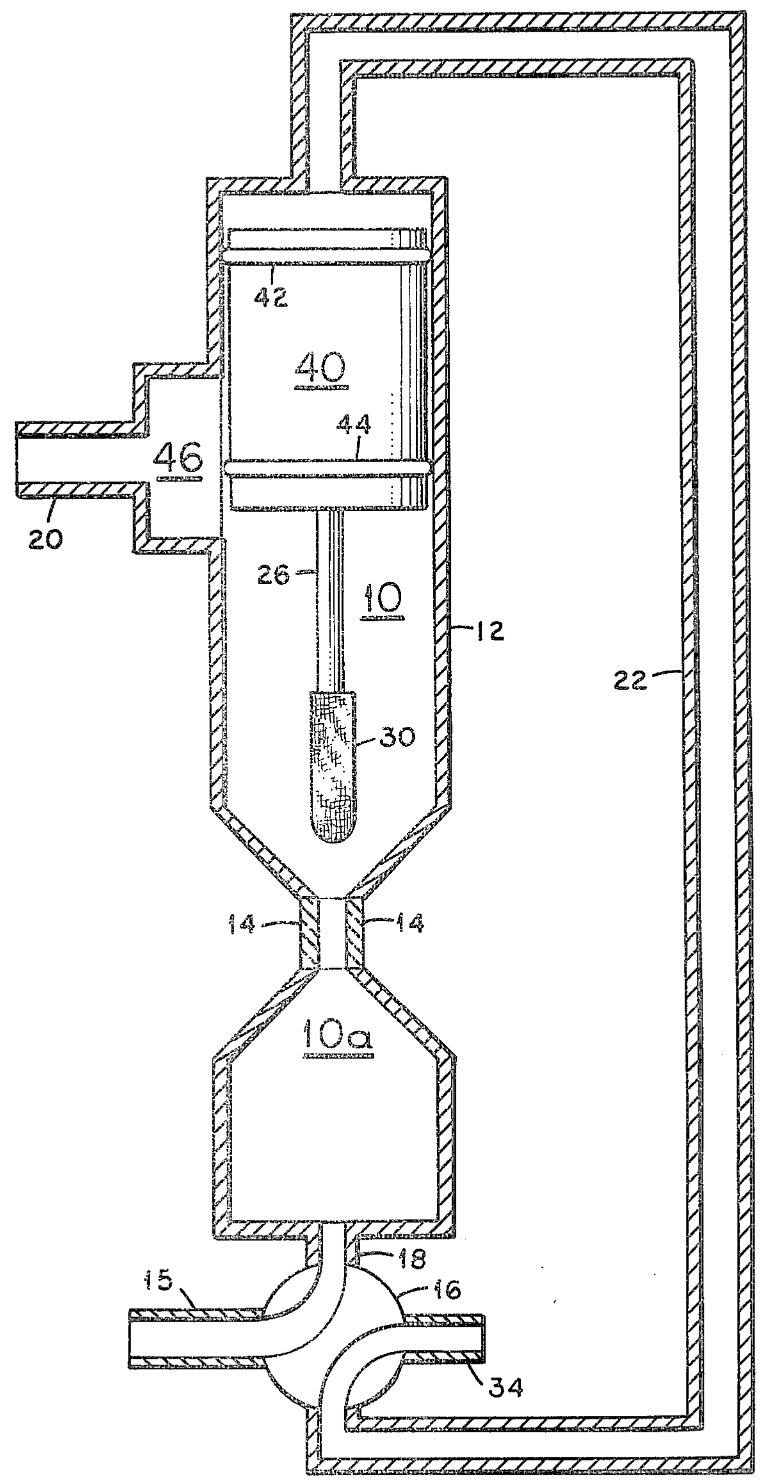
FIG. 3 is a sectional view of another embodiment of the invention.

FIG. 3 shows another modification of this invention in which the plunger consisting of the washers 24 and 32 on the rod 26 and guide wall 28 have been functionally replaced by an elongated cylinder or piston 40 having sealing devices such as "O" rings 42 and 44 mounted respectively at the top and bottom of the cylinder 40. Additionally, the outlet pipes 20 and 36 have been replaced by a single outlet chamber 46 for discharge of the liquid sample from the sample cell 10. While this embodiment has been shown only in the withdrawn position, it will be well understood by those skilled in the art how the embodiment of FIG. 3 operates when considered with the illustration of the embodiment shown in FIGS. 1 and 2.

With the arrangements disclosed the window cleaning operation may be simply performed by moving the valve 16 from one position as shown in FIG. 1 to a second position as shown in FIG. 2 and then return the valve 16 to its original position. The valve 16 has been shown as a rotary valve, however, it is to be understood that any type of valve arrangement may be utilized including sliding valves and/or electrically operated valves.

While two embodiments of the invention have been shown, it is to be understood that the embodiments shown herein are for the purpose of illustrating two forms of the invention and thus to enable those skilled in the art to adapt the invention in such ways as to meet the requirements of their application. While the embodiments have been described with respect to a sample cell for an analyzing device using a light source such as a laser it is to be understood that the invention is applicable to analyzers using any type of radiation that employ radiation transparent windows that require cleaning. It is to be understood that various other modifications may be made without departing from the scope of this invention.

What is claimed is:

1. A window cleaning arrangement for a radiation sensitive analysis device comprising:

an elongated chamber, a pair of windows located in opposite walls of said chamber, means for introducing a fluid to be analyzed into either end portion of said chamber, a plunger mounted within said chamber in sealing relation with said walls for movement axially of said chamber, window cleaning means located in a central portion of said chamber and connected to said plunger for movement past said windows with axial movement of said plunger, fluid valving means to alternately apply said fluid to be analyzed to one end portion of said chamber to move said window cleaning means into wiping engagement with said windows and to apply said fluid to the other end portion of said chamber to move said window cleaning means away from said windows, and fluid outlet means located in said wall of said chamber between said one end portion of said chamber and said windows.

2. A device for wiping an optical window of a sample cell of an optical instrument for examining a fluid sample in said sample cell and operable by the pressure of said liquid sample supplied to said sample cell comprising:

a source of said liquid sample, a piston mounted for longitudinal movement within said sample cell, window wiping means mounted to and movable with said piston into and out of wiping engagement with said optical window, and means for connecting said source of liquid sample alternately to opposite end portions of said sample cell for moving said window wiping means into and out of wiping engagement with said optical window.

3. Apparatus as claimed in claim 2 including:

a liquid waste pipe, and valving means for connecting an end portion of said sample cell to said waste pipe when the opposite end portion of said sample cell is connected to said source of liquid sample.

4. Apparatus as claimed in claim 2 including:

fluid sample outlet means in the side wall of said sample cell in flow communication with said end portion of said sample cell to which said source of liquid sample is connected after resulting movement of said window wiping means.

5. A self contained window cleaning arrangement for a fluid sample cell comprising:

a sample cell having side walls and end walls, said side walls being indented in a central portion of said sample cell, a pair of windows located in the indented opposite side walls of said cell for passage of light through said sample cell, a source of liquid to be analyzed, a first liquid inlet to said sample cell in one end wall of said cell, liquid outlet means from said sample cell located in said side wall of said sample cell, with said restricted area between said liquid outlet means and said first liquid inlet, a second liquid inlet located in the other end wall of said sample cell, a rod centrally located in said sample cell, window cleaning means for cleaning the inner surfaces of said windows attached to one end of said rod, first washer means of size and shape to form a seal with the side walls of said sample cell attached to the other end of said rod for moving said rod and said window cleaning means longitudinally in said cell into engagement with said windows and establishing flow communication between said second liquid inlet and said liquid outlet means when said source of supply of said liquid to be analyzed is connected to said second liquid inlet, second washer means attached to said rod between said first washer means and said window cleaning means for moving said rod and said window cleaning means out of engagement with said windows and establishing flow communication between said first liquid inlet and said liquid outlet means when said source of said liquid to be analyzed is connected to said first liquid inlet, a liquid waste outlet, and valving means for selectively connecting said source of supply of said liquid to said first liquid inlet and to said second liquid inlet and for simultaneously respectively connecting said liquid waste outlet to said second liquid inlet and said first liquid inlet.

* * * * *